US00PP23812P2

(12) United States Plant Patent
Kerley et al.

(10) Patent No.: US PP23,812 P2
(45) Date of Patent: Aug. 6, 2013

(54) ***PETUNIA* PLANT NAMED 'KERIVORYVEIN'**

(50) Latin Name: *Petunia×hybrida*
Varietal Denomination: Kerivoryvein

(76) Inventors: Priscilla Grace Kerley, Over (GB); David William Kerley, Over (GB); Timothy Edward Kerley, Longstanton (GB)

( * ) Notice: Subject to any disclaimer, the term of this patent is extended or adjusted under 35 U.S.C. 154(b) by 63 days.

(21) Appl. No.: 13/373,727

(22) Filed: Nov. 28, 2011

(51) Int. Cl.
*A01H 5/00* (2006.01)

(52) U.S. Cl.
USPC ..... Plt./356.15; Plt./356.1

(58) Field of Classification Search
USPC ..... Plt./356.1, 356.15
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Kerivoryvein', characterized by its mounding and semi-trailing growth habit; freely branching habit; early and freely flowering habit; medium-sized white-colored flowers with dark purple-colored centers and venation; and good garden performance.

2 Drawing Sheets

Botanical designation: *Petunia×hybrida.*
Cultivar denomination: 'KERIVORYVEIN'.

BACKGROUND OF THE INVENTION

The present invention relates to a new and distinct cultivar of *Petunia*, botanically known as *Petunia×hybrida* and hereinafter referred to by the name 'Kerivoryvein'.

The new *Petunia* plant is a product of a planned breeding program conducted by the Inventors in Cambridge, United Kingdom. The objective of the breeding program is to create new uniform *Petunia* plants with attractive flower coloration that are suitable for hanging basket containers.

The new *Petunia* plant originated from a cross-pollination made by the Inventors in August, 2007 in Cambridge, United Kingdom of a proprietary selection of *Petunia×hybrida* identified as code number 04-17-1, not patented, as the female, or seed, parent with a proprietary selection of *Petunia×hybrida* identified as code number 04-19-4, not patented, as the male, or pollen, parent. The new *Petunia* plant was discovered and selected by the Inventors as a single flowering plant within the progeny of the stated cross-pollination in a controlled greenhouse environment in Cambridge, United Kingdom in May, 2008.

Asexual reproduction of the new *Petunia* plant by terminal cuttings in a controlled greenhouse environment in Cambridge, United Kingdom since September, 2008 has shown that the unique features of this new *Petunia* plant are stable and reproduced true to type in successive generations.

SUMMARY OF THE INVENTION

Plants of the new *Petunia* have not been observed under all possible environmental conditions and cultural practices. The new *Petunia* plant's phenotype may vary somewhat with variations in environmental conditions and cultural practices such as temperature and light intensity without, however, any variance in genotype.

The following traits have been repeatedly observed and are determined to be the unique characteristics of 'Kerivoryvein'.

These characteristics in combination distinguish 'Kerivoryvein' as a new and distinct *Petunia* plant:

1. Mounding and semi-trailing growth habit.
2. Freely branching habit.
3. Early and freely flowering habit.
4. Medium-sized white-colored flowers with dark purple-colored centers and venation.
5. Good garden performance.

Plants of the new *Petunia* can be compared to plants of the female parent selection. Plants of the new *Petunia* differ from plants of the female parent selection in the following characteristics:

1. Plants of the new *Petunia* are more mounding than and not as trailing as plants of the female parent selection.
2. Plants of the new *Petunia* have larger flowers than plants of the female parent selection.
3. Flowers of plants of the new *Petunia* and the female parent selection differ slightly in venation color.

Plants of the new *Petunia* can be compared to plants of the male parent selection. Plants of the new *Petunia* differ from plants of the male parent selection in the following characteristics:

1. Plants of the new *Petunia* are more mounding than and not as upright as plants of the male parent selection.
2. Plants of the new *Petunia* have smaller flowers than plants of the male parent selection.
3. Flowers of plants of the new *Petunia* and the male parent selection differ in flower color as plants of the male parent selection have light yellow-colored flowers with reddish brown-colored venation.

Plants of the new *Petunia* can be compared to plants of the Petunia 'Kakegawa S30', disclosed in U.S. Plant Pat. No. 13,862. In side-by-side comparisons conducted in Cambridge, United Kingdom, plants of the new *Petunia* differed from plants of 'Kakegawa S30' in the following characteristics:

1. Plants of the new *Petunia* were more upright than and not as trailing as plants of 'Kakegawa S30'.
2. Plants of the new *Petunia* had larger leaves than plants of 'Kakegawa S30'.

3. Plants of the new *Petunia* and 'Kakegawa S30' differed in flower color as plants of 'Kakegawa S30' had solid white-colored flowers.

Plants of the new *Petunia* can also be compared to plants of the *Petunia* 'Lanbor', disclosed in U.S. Plant Pat. No. 16,144. In side-by-side comparisons conducted in Cambridge, United Kingdom, plants of the new *Petunia* differed from plants of 'Lanbor' in the following characteristics:

1. Plants of the new *Petunia* were less vigorous than plants of 'Lanbor'.
2. Plants of the new *Petunia* and 'Lanbor' differed in flower color as plants of 'Lanbor' had light purple-colored flowers with dark purple-colored centers and venation.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet comprises a side perspective view of typical plants of 'Kerivoryvein' grown in a container.

The photograph on the second sheet is a close-up view of a typical flower of 'Kerivoryvein'.

DETAILED BOTANICAL DESCRIPTION

The aforementioned photographs and following observations, measurements and values describe plants grown in 20-cm containers during the summer in a glass-covered greenhouse in Cambridge, United Kingdom and under commercial cultural practices. During the production of the plants, day temperatures ranged from 18° C. to 28° C., night temperatures ranged from 14° C. to 20° C. and light levels averaged 50 kilolux. Plants were pinched one time and were ten weeks old when the photographs and description were taken. In the following description, color references are made to The Royal Horticultural Society Colour Chart, 1995 Edition, except where general terms of ordinary dictionary significance are used.

Botanical classification: *Petunia×hybrida* 'Kerivoryvein'.

Parentage:

*Female, or seed, parent*.—Proprietary selection of *Petunia×hybrida* identified as code number 04-17-1, not patented.

*Male, or pollen, parent*.—Proprietary selection of *Petunia×hybrida* identified as code number 04-19-4, not patented.

Propagation:

*Type*.—By terminal cuttings.

*Time to initiate roots, summer*.—About seven days at temperatures of about 20° C.

*Time to initiate roots, winter*.—About ten days at temperatures of about 20° C.

*Time to produce a rooted young plant, summer*.—About 25 days at temperatures of about 20° C.

*Time to produce a rooted young plant, winter*.—About 35 days at temperatures of about 15° C.

*Root description*.—Fine, fibrous; white in color.

*Rooting habit*.—Freely branching; medium density.

Plant description:

*Plant and growth habit*.—Mounding and semi-trailing growth habit; freely branching habit with about six primary lateral branches developing per plant; pinching enhances lateral branch development; moderately vigorous growth habit.

*Plant height*.—About 18 cm to 21 cm.

*Plant diameter*.—About 74 cm.

Lateral branch description:

*Length*.—About 38 cm.

*Diameter*.—About 4.8 mm.

*Internode length*.—About 3.2 cm.

*Aspect*.—Initially upright to semi-trailing.

*Texture*.—Pubescent.

*Color*.—Close to 143B and 144A.

Foliage description:

*Arrangement*.—Before flowering, alternate, simple; after flowering, opposite, simple.

*Length*.—About 4.7 cm.

*Width*.—About 3 cm.

*Shape*.—Broadly elliptic.

*Apex*.—Acute.

*Base*.—Acute.

*Margin*.—Entire.

*Texture, upper and lower surfaces*.—Slightly pubescent.

*Venation pattern*.—Pinnate; arcuate.

*Color*.—Developing leaves, upper surface: Slightly lighter than 147A. Developing leaves, lower surface: Slightly lighter than 147B. Fully expanded leaves, upper surface: Darker than 147A; venation, close to 137B. Fully expanded leaves, lower surface: Close to 147B; venation, close to 144B.

*Petiole length*.—About 5.7 mm.

*Petiole diameter*.—About 3.5 mm.

*Petiole texture, upper and lower surfaces*.—Pubescent.

*Petiole color, upper and lower surfaces*.—Close to 144A to 144B.

Flower description:

*Flower arrangement and habit*.—Single-type salverform flowers; singly arising from leaf axils; freely flowering habit with usually about 60 flowers developing per plant; flowers face mostly outwardly.

*Fragrance*.—Slightly fragrant, pleasant.

*Natural flowering season*.—Plants flower continuously during the summer in the United Kingdom.

*Flower longevity*.—Individual flowers last about four to eight days on the plant; flowers persistent.

*Flower diameter*.—About 6.5 cm to 6.8 cm.

*Flower depth (height)*.—About 3.2 cm to 4.7 cm.

*Flower bud*.—Shape: Oblong. Length: About 4 cm. Diameter: About 7 mm. Color: Towards the base, close to 144C; towards the apex, close to 144D; venation, close to 187A.

*Corolla*.—Arrangement: Five petals fused at the base and opening into a flared trumpet. Petal length from throat: About 2.5 cm to 3.1 cm. Petal lobe width: About 3.2 cm to 3.5 cm. Petal shape: Spatulate. Petal apex: Obtuse. Petal margin: Entire. Petal texture, upper surface: Smooth, glabrous. Petal texture, lower surface: Slightly pubescent. Throat texture: Smooth, glabrous. Tube texture: Pubescent. Petal color: When opening, upper surface: Close to 155D; venation, close to 187A. When opening, lower surface: Close to 11D; lateral venation, close to 187A to 187B; main veins, close to 199A. Fully opened, upper surface:

Close to 155B; lateral venation, darker than 79A; main veins, close to 200A becoming lighter, close to 79D, towards the margins; throat, close to 202A. Fully opened, lower surface: Close to 155B; lateral venation, close to 79A to 79D; main veins, close to 199B.

*Calyx*.—Arrangement: One star-shaped calyx tube with five sepals fused at the base per flower. Sepal length: About 1.7 cm to 2.1 cm. Sepal width: About 3 mm to 6 mm. Sepal shape: Narrowly oblong. Sepal apex: Obtuse. Sepal margin: Entire. Sepal texture, upper and lower surfaces: Pubescent, coarse. Color, immature and mature, upper surface: Close to 147A. Color, immature and mature, lower surface: Close to 146A.

*Peduncles*.—Length: About 2.5 cm to 2.9 cm. Diameter: About 2 mm. Angle: About 45° from the stem axis. Strength: Strong. Texture: Pubescent. Color: Close to 144A.

*Reproductive organs*.—Stamens: Quantity: Five per flower. Anther shape: Oblong. Anther size: About 2 mm by 3 mm. Anther color: Close to 11C. Pollen amount: Abundant. Pollen color: Close to 11D. Pistils: Quantity: One per flower. Pistil length: About 2.2 cm. Style length: About 1.7 cm. Style color: Close to 145D. Stigma shape: Oval. Stigma color: Close to 144A. Ovary color: Close to 144A. Seeds and fruits: Seed and fruit development have not been observed on plants of the new *Petunia*.

Garden performance: Plants of the new *Petunia* have been observed to have good garden performance and tolerate wind, rain and temperatures ranging from about 4° C. to about 40° C.

Pathogen & pest resistance: Plants of the new *Petunia* have not been observed to be resistant to pathogens and pests common to *Petunia*.

It is claimed:

1. A new and distinct *Petunia* plant named 'Kerivoryvein' as illustrated and described.

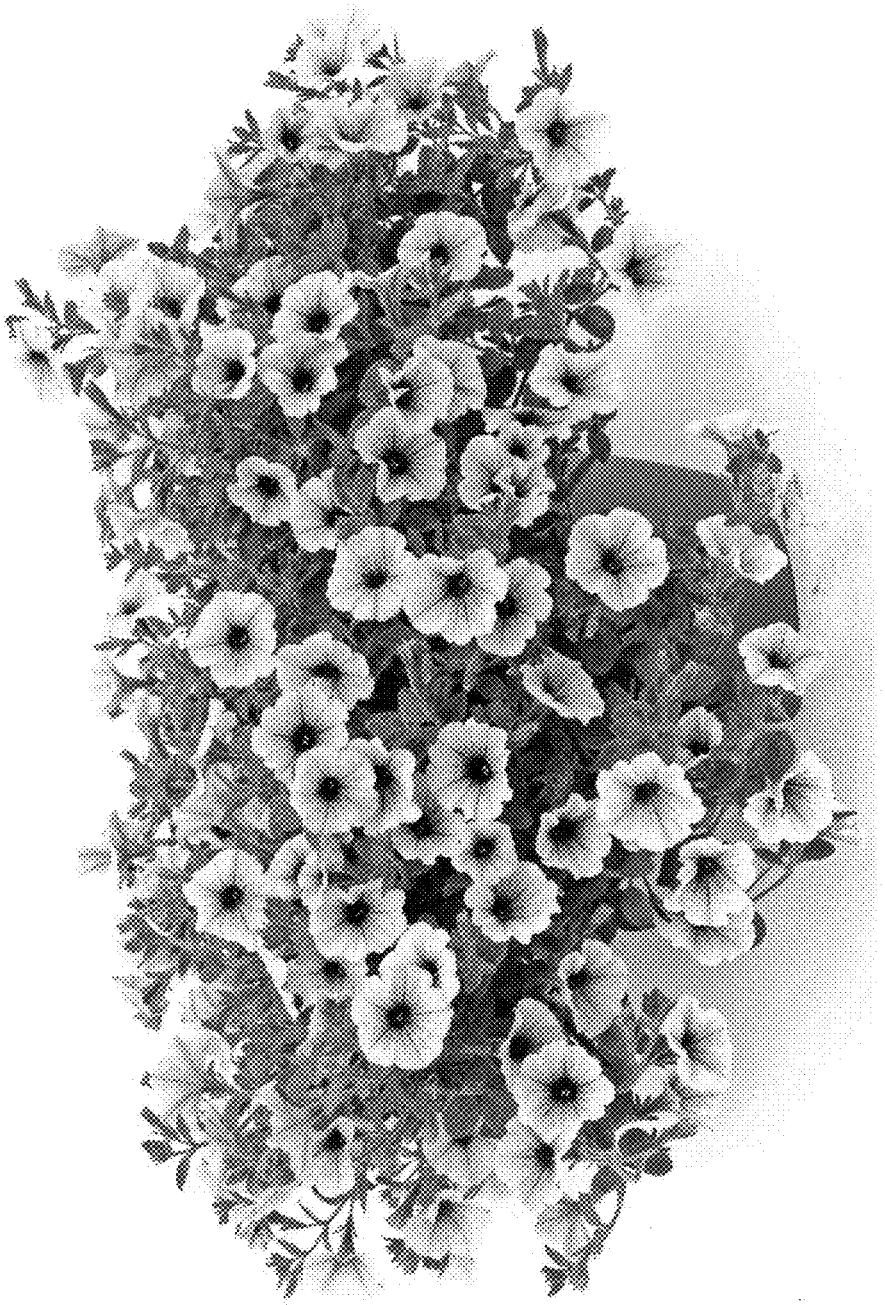

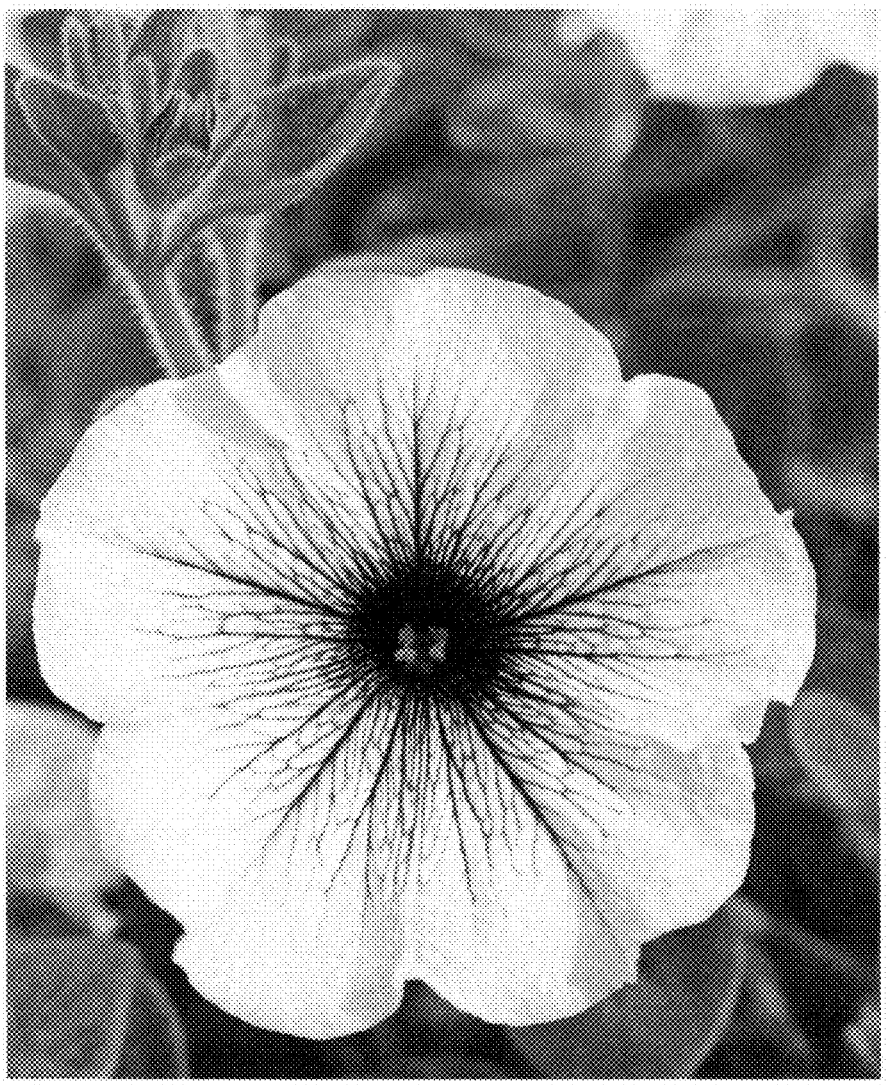

* * * * *